US008449608B2

(12) United States Patent
Brunnett et al.

(10) Patent No.: US 8,449,608 B2
(45) Date of Patent: May 28, 2013

(54) TRICUSPID RING

(75) Inventors: William C. Brunnett, Mission Viejo, CA (US); Alison S. Curtis, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 68 days.

(21) Appl. No.: 13/010,079

(22) Filed: Jan. 20, 2011

(65) Prior Publication Data
US 2011/0184511 A1 Jul. 28, 2011

Related U.S. Application Data

(60) Provisional application No. 61/297,686, filed on Jan. 22, 2010.

(51) Int. Cl.
*A61F 2/24* (2006.01)
(52) U.S. Cl.
USPC ........................................ 623/2.36; 623/2.37
(58) Field of Classification Search
USPC ............................................... 623/2.36–2.37
See application file for complete search history.

(56) References Cited

U.S. PATENT DOCUMENTS

| | | | |
|---|---|---|---|
| 3,656,185 A | 4/1972 | Carpentier | |
| 4,055,861 A | 11/1977 | Carpentier et al. | |
| 4,164,046 A | 8/1979 | Cooley | |
| 4,217,665 A | 8/1980 | Bex et al. | |
| 4,602,911 A | 7/1986 | Ahmadi et al. | |
| 5,041,130 A | 8/1991 | Cosgrove et al. | |
| 5,061,277 A | 10/1991 | Carpentier et al. | |
| 5,064,431 A | 11/1991 | Gilbertson et al. | |
| 5,104,407 A | 4/1992 | Lam et al. | |
| 5,201,880 A | 4/1993 | Wright et al. | |
| 5,258,021 A | 11/1993 | Duran | |
| 5,306,296 A | 4/1994 | Wright et al. | |
| 5,450,860 A | 9/1995 | O'Connor | |
| 5,496,336 A | 3/1996 | Cosgrove et al. | |
| 5,593,435 A | 1/1997 | Carpentier et al. | |

(Continued)

FOREIGN PATENT DOCUMENTS

| | | |
|---|---|---|
| EP | 0 338 994 | 10/1989 |
| EP | 1 034 753 | 9/2000 |

OTHER PUBLICATIONS

Adams, David, et al., "Large Annuloplasty Rings Facilitate Mitral Valve Repair in Barlow's Disease," Society of Thoracic Surgeons 42$^{nd}$ Annual Meeting, Jan. 30-Feb. 1, 2006.

(Continued)

*Primary Examiner* — David H Willse
*Assistant Examiner* — Tiffany Shipmon
(74) *Attorney, Agent, or Firm* — AnneMarie Kaiser; Guy Cumberbatch

(57) ABSTRACT

A prosthetic tricuspid remodeling annuloplasty ring having two free ends can be configured to be stiff in the XY plane and relatively flexible along the Z axis. A tricuspid ring can be provided with a substantially elliptical shape in the XY plane, and a saddle shape in the Z direction. Disclosed tricuspid rings can include an inner core, an elastomeric interface, and an outer fabric covering. In some embodiments, the inner core can include a plurality of stacked layers of different materials. In some embodiments, the inner core can be formed of a single material and sized specifically to create a tricuspid ring that has a greater stiffness in the XY plane than along the Z axis.

24 Claims, 8 Drawing Sheets

U.S. PATENT DOCUMENTS

| | | |
|---|---|---|
| 5,607,471 A | 3/1997 | Seguin et al. |
| 5,669,919 A | 9/1997 | Sanders et al. |
| 5,674,279 A | 10/1997 | Wright et al. |
| 5,776,189 A | 7/1998 | Khalid |
| 5,824,066 A | 10/1998 | Gross |
| 5,888,240 A | 3/1999 | Carpentier et al. |
| 5,972,030 A | 10/1999 | Garrison et al. |
| 6,102,945 A | 8/2000 | Campbell |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,332,893 B1 | 12/2001 | Mortier et al. |
| 6,368,348 B1 | 4/2002 | Gabbay |
| 6,391,054 B2 | 5/2002 | Carpentier et al. |
| 6,406,493 B1 | 6/2002 | Tu et al. |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,908,482 B2 | 6/2005 | McCarthy |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,101,395 B2 | 9/2006 | Tremulis et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,294,148 B2 | 11/2007 | McCarthy |
| 7,608,103 B2 | 10/2009 | McCarthy |
| 2002/0173841 A1* | 11/2002 | Ortiz et al. .................... 623/2.11 |
| 2003/0033009 A1 | 2/2003 | Gabbay |
| 2003/0040793 A1 | 2/2003 | Marquez |
| 2003/0045929 A1* | 3/2003 | McCarthy et al. ........... 623/2.37 |
| 2004/0249452 A1 | 12/2004 | Adams et al. |
| 2004/0249453 A1 | 12/2004 | Cartledge et al. |
| 2005/0131533 A1 | 6/2005 | Alfieri et al. |
| 2005/0256567 A1 | 11/2005 | Lim et al. |
| 2005/0256568 A1 | 11/2005 | Lim et al. |
| 2005/0267572 A1 | 12/2005 | Schoon et al. |
| 2005/0278022 A1 | 12/2005 | Lim |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025858 A1 | 2/2006 | Alameddine |
| 2006/0030885 A1 | 2/2006 | Hyde |
| 2007/0162111 A1 | 7/2007 | Fukamachi et al. |
| 2009/0036979 A1 | 2/2009 | Redmond et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192606 A1 | 7/2009 | Gloss et al. |

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Carpentier, et al. "The 'Physio-Ring': An Advanced Concept in Mitral Valve Annuloplasty," Society of Thoracic Surgeons $31^{st}$ Annual meeting, Jan. 30-Feb. 2, 1995.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Carpentier, et al., *Reconstructive Valve Surgery*, Chapter 19—Reconstructive Techniques, ISBN No. 978-0-7216-9168-8, Sanders Elsevier Publishing, Maryland Heights, Missouri, 2010.

D.C. Miller, IMR Redux—To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Miller, D. Craig, M.D., "Ischemic Mitral Regurgitation Redux—to Repair or Replace?", The Journal of Thoracic & Cardiovascular Surgery, Dec. 2001, vol. 122, No. 6, pp. 1059-1062.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association © 2005; ISSN: 1524-4539.

International Search Report in corresponding PCT application No. PCT/US2011/021996 dated Oct. 14, 2011.

* cited by examiner

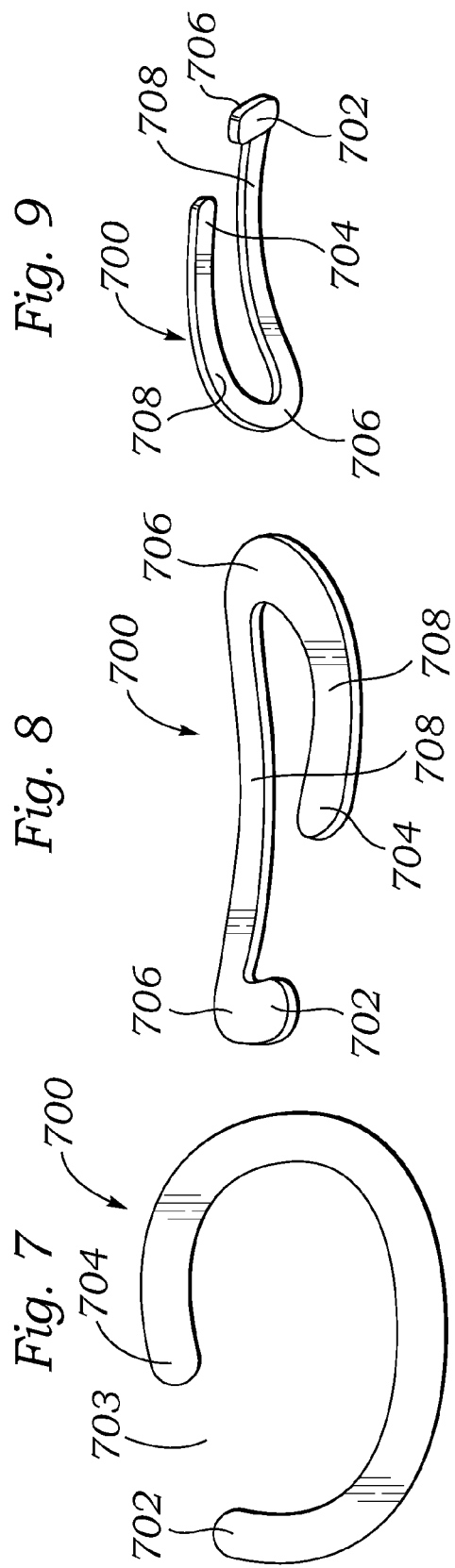

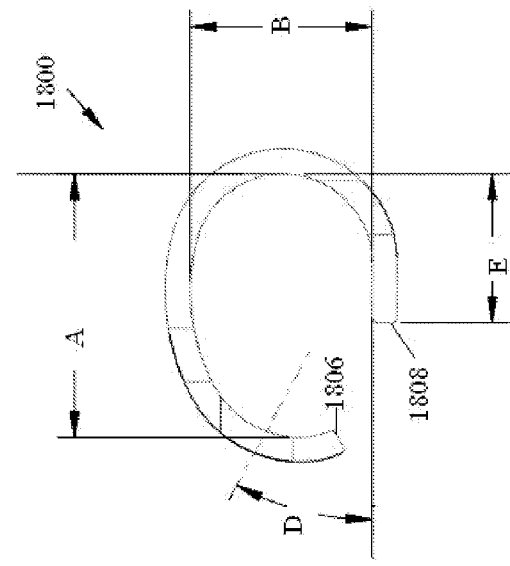
FIG. 18
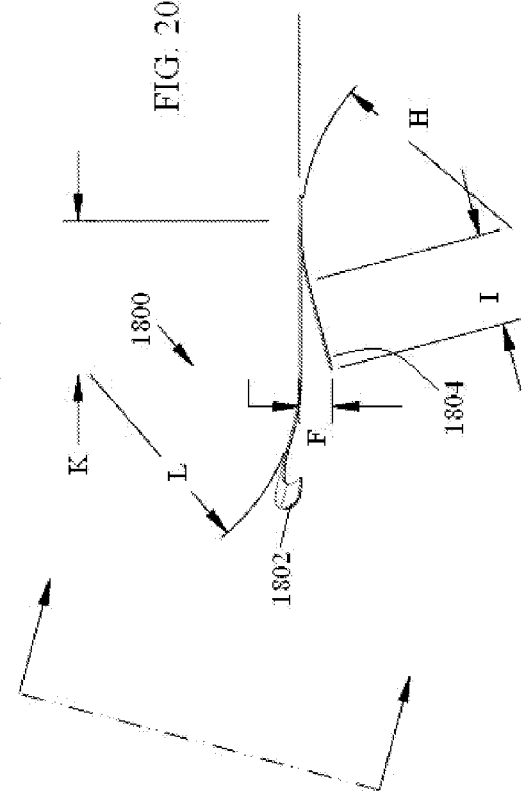
FIG. 20
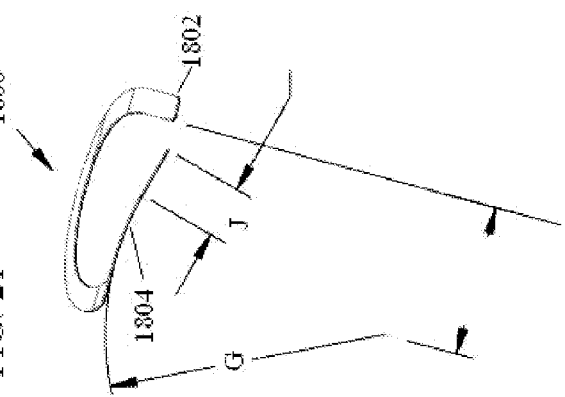
FIG. 19
FIG. 21

TRICUSPID RING

RELATED APPLICATIONS

The present application claims priority under 35 U.S.C. § 119 to U.S. Provisional Application No. 61/297,686, filed on Jan. 22, 2010, which is incorporated herein by reference in its entirety.

FIELD

The present invention relates generally to medical devices and particularly to a tricuspid annuloplasty ring.

BACKGROUND

In vertebrate animals, the heart is a hollow muscular organ having four pumping chambers: the left and right atria and the left and right ventricles, each provided with its own one-way valve. The native heart valves are identified as the aortic, mitral (or bicuspid), tricuspid, and pulmonary, and each is mounted in an annulus comprising dense fibrous rings attached either directly or indirectly to the atrial and ventricular muscle fibers. Each annulus defines a flow orifice.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed (regurgitation). Valve disease can be severely debilitating and even fatal if left untreated.

A healthy tricuspid valve annulus is substantially ovoid in the XY plane, having a bimodal saddle shape in the Z direction. A diseased tricuspid valve annulus is often substantially flat in the Z direction, and can experience severe distension in the XY plane. During the cardiac cycle, a healthy valve annulus typically expands in the XY direction, as well as slightly accentuates the saddle in the Z direction. In diseased valves, there is often suppressed orifice expansion, as well as substantially no saddle accentuation during the cardiac cycle.

Various surgical techniques may be used to repair a diseased or damaged valve. In a valve replacement operation, the damaged leaflets are excised and the annulus sculpted to receive a replacement valve. Another less drastic method for treating defective valves is through repair or reconstruction, which is typically used on minimally calcified valves. One repair technique is remodeling annuloplasty, in which the deformed valve annulus is reshaped by attaching a prosthetic annuloplasty repair segment or ring to the valve annulus. The annuloplasty ring is designed to support the functional changes that occur during the cardiac cycle: maintaining coaptation and valve integrity to prevent reverse flow while permitting good hemodynamics during forward flow.

An annuloplasty ring typically comprises an inner substrate of a metal such as rods or bands of stainless steel or titanium, or a flexible material such as silicone rubber or Dacron cordage, covered with a biocompatible fabric or cloth to allow the ring to be sutured to the fibrous annulus tissue. Annuloplasty rings may be stiff or flexible, split or continuous, and may have a variety of shapes, including circular, D-shaped, C-shaped, or kidney-shaped. Examples are seen in U.S. Pat. Nos. 5,041,130, 5,104,407, 5,201,880, 5,258,021, 5,607,471, 6,187,040, and 6,908,482.

FIG. 1 shows a schematic representation of the anatomic orientation of the heart, illustrating the atrioventricular (AV) junctions within the heart and the body in the left anterior oblique projection. The body is viewed in the upright position and has three orthogonal axes: superior-inferior, posterior-anterior, and right-left.

FIG. 2 is a cutaway view of the heart from the front, or anterior, perspective, with most of the primary structures marked. As is well known, the pathway of blood in the heart is from the right atrium to the right ventricle through the tricuspid valve, to and from the lungs, and from the left atrium to the left ventricle through the mitral valve. The present application has particular relevance to the repair of the tricuspid valve, which regulates blood flow between the right atrium and right ventricle, although certain aspects may apply to repair of other of the heart valves. The tricuspid and mitral valves together define the AV junctions.

As seen in FIG. 2, four structures embedded in the wall of the heart conduct impulses through the cardiac muscle to cause first the atria then the ventricles to contract. These structures are the sinoatrial node (SA node), the atrioventricular node (AV node), the bundle of His, and the Purkinje fibers. On the rear wall of the right atrium is a barely visible knot of tissue known as the sinoatrial, or SA node. This tiny area is the control of the heart's pacemaker mechanism. Impulse conduction normally starts in the SA node. It generates a brief electrical impulse of low intensity approximately 72 times every minute in a resting adult. From this point, the impulse spreads out over the sheets of tissue that make up the two atria, exciting the muscle fibers as it does so. This causes contraction of the two atria and thereby thrusts the blood into the empty ventricles. The impulse quickly reaches another small, specialized knot of tissue known as the AV node, located between the atria and the ventricles. This node delays the impulse for about 0.07 seconds, which is exactly enough time to allow the atria to complete their contractions. When the impulses reach the AV node, they are relayed by way of the several bundles of His and Purkinje fibers to the ventricles, causing them to contract. As those of skill in the art are aware, the integrity and proper functioning of the conductive system of the heart is critical for good health.

FIG. 3 is a schematic view of the tricuspid valve orifice seen from its inflow side (from the right atrium), with the peripheral landmarks labeled as: antero-septal commissure, anterior leaflet, posterior commissure, posterior leaflet, postero-septal commissure, and septal leaflet. Contrary to traditional orientation nomenclature, the tricuspid valve is nearly vertical, as reflected by these sector markings. From the same viewpoint, the tricuspid valve is shown surgically exposed in FIG. 4 with an annulus 22 and three leaflets 24a, 24b, 24c extending inward into the flow orifice. Chordae tendineae 26 connect the leaflets to papillary muscles located in the right ventricle to control the movement of the leaflets. The tricuspid annulus 22 is an ovoid-shaped fibrous ring at the base of the valve that is less prominent than the mitral annulus, but larger in circumference.

Reflecting their true anatomic location, the three leaflets in FIG. 4 are identified as septal 24a, anterior 24b, and posterior (or "mural") 24c. The leaflets join together over three prominent zones of apposition, and the peripheral intersections of these zones are usually described as commissures 28. The leaflets 24 are tethered at the commissures 28 by the fan-shaped chordae tendineae 26 arising from prominent papillary muscles originating in the right ventricle. The septal leaflet 24a is the site of attachment to the fibrous trigone, the fibrous "skeletal" structure within the heart. The anterior leaflet 24b, the largest of the 3 leaflets, often has notches. The posterior leaflet 24c, the smallest of the 3 leaflets, usually is scalloped.

The ostium 30 of the right coronary sinus opens into the right atrium, and the tendon of Todaro 32 extends adjacent thereto. The AV node 34 and the beginning of the bundle of His 36 are located in the supero-septal region of the tricuspid valve circumference. The AV node 34 is situated directly on the right atrial side of the central fibrous body in the muscular portion of the AV septum, just superior and anterior to the ostium 30 of the coronary sinus 30. Measuring approximately 1.0 mm×3.0 mm×6.0 mm, the node is flat and generally oval shaped. The AV node is located at the apex of the triangle of Koch 38, which is formed by the tricuspid annulus 22, the ostium 30 of the coronary sinus, and the tendon of Todaro 32. The AV node 34 continues on to the bundle of His 36, typically via a course inferior to the commissure 28 between the septal 24a and anterior 24b leaflets of the tricuspid valve; however, the precise course of the bundle of His 36 in the vicinity of the tricuspid valve may vary. Moreover, the location of the bundle of His 36 may not be readily apparent from a resected view of the right atrium because it lies beneath the annulus tissue.

The triangle of Koch 30 and tendon of Todaro 32 provide anatomic landmarks during tricuspid valve repair procedures. A major factor to consider during surgery is the proximity of the conduction system (AV node 34 and bundle of His 36) to the septal leaflet 24a. Of course, surgeons must avoid placing sutures too close to or within the AV node 34. C-shaped rings are good choices for tricuspid valve repairs because they allow surgeons to position the break in the ring adjacent the AV node 34, thus avoiding the need for suturing at that location.

One prior art rigid C-shaped ring is the Carpentier-Edwards Classic® Tricuspid Annuloplasty Ring sold by Edwards Lifesciences Corporation of Irvine, Calif., which is seen in FIGS. 5A and 5B. Although not shown, the planar ring 40 has an inner titanium core covered by a layer of silicone and fabric. Rings for sizes 26 mm through 36 mm in 2 mm increments have outside diameters (OD) between 31.2-41.2 mm, and inside diameters (ID) between 24.3-34.3 mm. These diameters are taken along the "diametric" line spanning the greatest length across the ring because that is the conventional sizing parameter. A gap G between free ends 42a, 42b in each provides the discontinuity to avoid attachment over the AV node 34. The gap G for the various sizes ranges between about 5-8 mm, or between about 19%-22% of the labeled size. As seen in the implanted view of FIG. 6, the gap G is sized just larger than the AV node 34. The ring is typically attached to the heart using single loop interrupted sutures along the outer edge of the ring. Despite the gap between the ends of the ring, some surgeons are uncomfortable passing sutures so close to the conductive AV node 34, particularly considering the additional concern of the bundle of His 36.

A flexible C-shaped tricuspid ring is sold under the name Sovering™ by Sorin Biomedica Cardio S.p.A. of Via Crescentino, Italy. The Sovering™ is made with a radiopaque silicone core covered with a knitted polyester (PET) fabric so as to be totally flexible. Rings for sizes 28 mm through 36 mm in 2 mm increments have outside diameters (OD) between 33.8-41.8 mm, and inside diameters (ID) between 27.8-35.8 mm. As with other tricuspid rings, a gap between the free ends provides a discontinuity to avoid attachment over the AV node. The gap for the various sizes ranges of the Sovering™ ranges between about 18-24 mm, or between about 60%-70% of the labeled size. Although this gap helps avoid passing sutures close to the conductive AV node 34 and bundle of His 36, the ring is designed to be attached at the commissures on either side of the septal leaflet and thus no support is provided on the septal side.

Whether totally flexible, rigid, or semi-rigid, annuloplasty rings have sometimes been associated with a certain degree of arrhythmia. Prior art annuloplasty rings have also been associated with a 10% to 15% incidence of ring dehiscence and/or conduction tissue disturbance at 10 years post implantation. Additionally, prior art annuloplasty rings have been associated with residual tricuspid regurgitation after implantation. Rigid annuloplasty rings, such as the Classic® Tricuspid Annuloplasty Ring, can reshape the native annulus in the XY plane and optimize leaflet coaptation, but the rigidity of the ring forces the annulus to conform to the ring in the Z direction, thus increasing stress in the native valve tissue. Flexible annuloplasty rings can be flexible enough to conform to native valve anatomy, but disadvantageously do not reshape the native valve anatomy. Thus, despite numerous designs presently available or proposed in the past, there is a need for an improved prosthetic tricuspid ring that addresses these and other issues with prior art tricuspid rings.

SUMMARY

Disclosed embodiments of a tricuspid ring can at least partially restore the correct anatomy of the tricuspid valve annulus and/or the right ventricle. Tricuspid rings according to the present disclosure can be configured to be stiff or rigid in the XY plane (e.g., the plane of the annulus) and semi-flexible along the Z axis, or in the Z direction. The stiffness in the XY plane can allow embodiments of the disclosed tricuspid ring to resize the native valve annulus, such as by reshaping a dilated tricuspid valve that is regurgitating. The semi-flexibility along the Z axis can allow some embodiments of a tricuspid ring to conform to the natural shape of the native annulus, thereby reducing stress on the sutures securing the tricuspid ring in place. Tricuspid rings of the present disclosure can thereby reduce the likelihood of dehiscence in some embodiments.

One embodiment of a tricuspid ring for use in an annuloplasty procedure can comprise an inner core comprising a plurality of layers stacked along the Z axis, an elastomeric interface at least partially covering the inner core, and a biocompatible flexible layer at least partially covering the elastomeric interface. The tricuspid ring can be configured to be rigid in the XY plane and flexible along the Z axis.

In some embodiments, the plurality of layers can comprise at least one structural layer and at least one interface layer. The structural layers can comprise at least one material selected from the group consisting of Elgiloy, Nitinol, titanium, stainless steel, cobalt chromium, and alloys thereof. The interface layers can comprise at least one material selected from the group consisting of polyester, PET, PEEK, PTFE, polycarbonate, polysulfone, and polyphenylsulfone.

The structural layers and the interface layers can be arranged in an alternating stack along the Z axis. In specific embodiments, the plurality of layers can comprise four structural layers and three interface layers, with each of the interface layers being arranged between two structural layers (e.g., the stack forming the inner core can have a structural layer on top, followed by an interface layer, a second structural layer, a second interface layer, a third structural layer, a third interface layer, and a fourth structural layer on the bottom). In other embodiments, more or fewer layers (e.g., more or fewer structural layers and/or more or fewer interface layers) can be included in the stack forming the inner core.

In some embodiments, each of the plurality of layers can be substantially the same size. In some embodiments, each of the layers can comprise a structural portion and a shim portion. The structural portions can comprise at least one material selected from the group consisting of Elgiloy, Nitinol, titanium, stainless steel, cobalt chromium, and alloys thereof. The shim portions can comprise at least one material selected from the group consisting of polyester, PET, PEEK, PTFE, polycarbonate, polysulfone, and polyphenylsulfone. The structural portions of adjacent layers can be arranged to at least partially overlap. In some embodiments, the structural portion of any given layer can be arranged to overlap a portion of the structural portion of the adjacent layer.

In some embodiments, the structural portion of any given layer can be bigger than the shim portion of any adjacent layer. In some embodiments, the plurality of layers can comprise a plurality of pairs of layers, each pair of layers comprising a first layer and a second layer. The structural portion of the second layer can be bigger than the shim portion of the first layer, the shim portion of the first layer can be bigger than the structural portion of the first layer, and the structural portion of the first layer can be bigger than the shim portion of the second layer. The shim portion of the first layer can be arranged to overlap more of the structural portion of the second layer than is the structural portion of the second layer. In some embodiments, the shim portion of any given layer and the shim portion of the adjacent layer do not overlap. For example, the shim portion of the first layer and the shim portion of the second layer do not overlap in some embodiments.

The elastomeric interface can comprise, for example, silicone overmolding and/or silicone tubing. The biocompatible flexible layer can comprise fabric or cloth, such as a polyester. In some embodiments, the inner core can be contained within the elastomeric interface without any weld points. In other embodiments, at least one weld point can couple the layers of the inner core together. For example, at least one weld point can be provided on overlapping parts of the structural portions of adjacent layers in some embodiments.

Some embodiments of a tricuspid ring can include a sewing cuff that can facilitate suturing of the tricuspid ring in place within a patient's native valve.

Embodiments of a tricuspid ring can be configured such that a gap exists between a first free end and a second free end, the tricuspid ring having a saddle shape (e.g., a bimodal saddle shape) having at least one high point and at least one low point.

Another embodiment of a tricuspid ring for use in an annuloplasty procedure can comprise an inner core having a rectangular cross section defined by a thickness and a width, an elastomeric interface at least partially covering the inner core, and a biocompatible flexible layer at least partially covering the elastomeric interface. The inner core can be configured such that its width and thickness result in a stiffness in the XY plane that is between approximately 10 times and approximately 100 times greater than the stiffness along the Z axis. For example, in one embodiment, the stiffness in the XY plane can be about 25 times the stiffness along the Z axis or greater. Thus, the tricuspid ring can be configured to be rigid in the XY plane and flexible along the Z axis. The tricuspid ring can further comprise a sewing cuff.

While the term "tricuspid ring" is used throughout this disclosure, embodiments include both continuous, complete rings and discontinuous rings, with two free ends separated by a gap.

The foregoing and other objects, features, and advantages of the invention will become more apparent from the following detailed description, which proceeds with reference to the accompanying figures.

BRIEF DESCRIPTION OF THE DRAWINGS

FIG. 7 is a plan view of one embodiment of a tricuspid ring according to the present disclosure.

FIG. 8 is a perspective view of the tricuspid ring of FIG. 7.

FIG. 9 is another perspective view of the tricuspid ring of FIG. 7.

FIG. 18 shows a plan view of one embodiment of a tricuspid ring.

FIG. 19 shows a side elevation view of the tricuspid ring of FIG. 18.

FIG. 20 shows a side elevation view of the tricuspid ring of FIG. 18.

FIG. 21 shows a perspective view of the tricuspid ring of FIG. 18.

DETAILED DESCRIPTION

Figure 1:
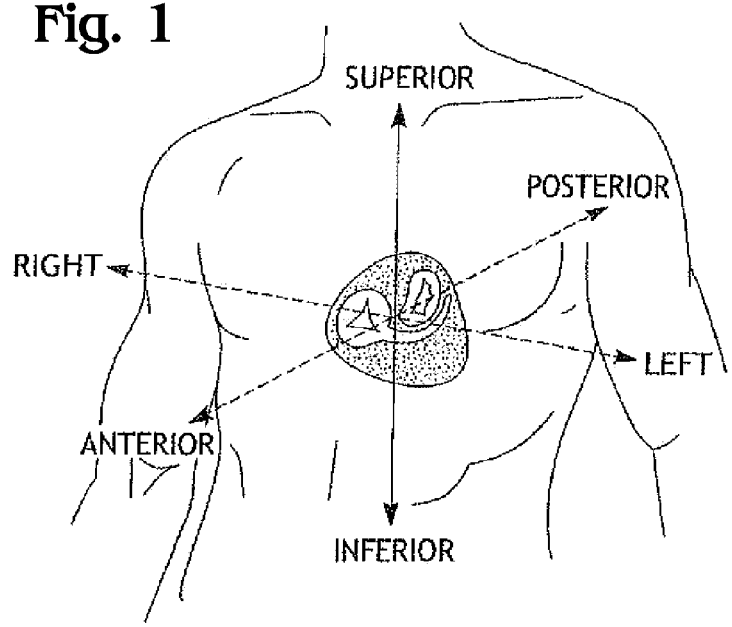
FIG. 1 is a schematic representation of the AV junctions within the heart and the body in the left anterior oblique projection.
Figure 2:
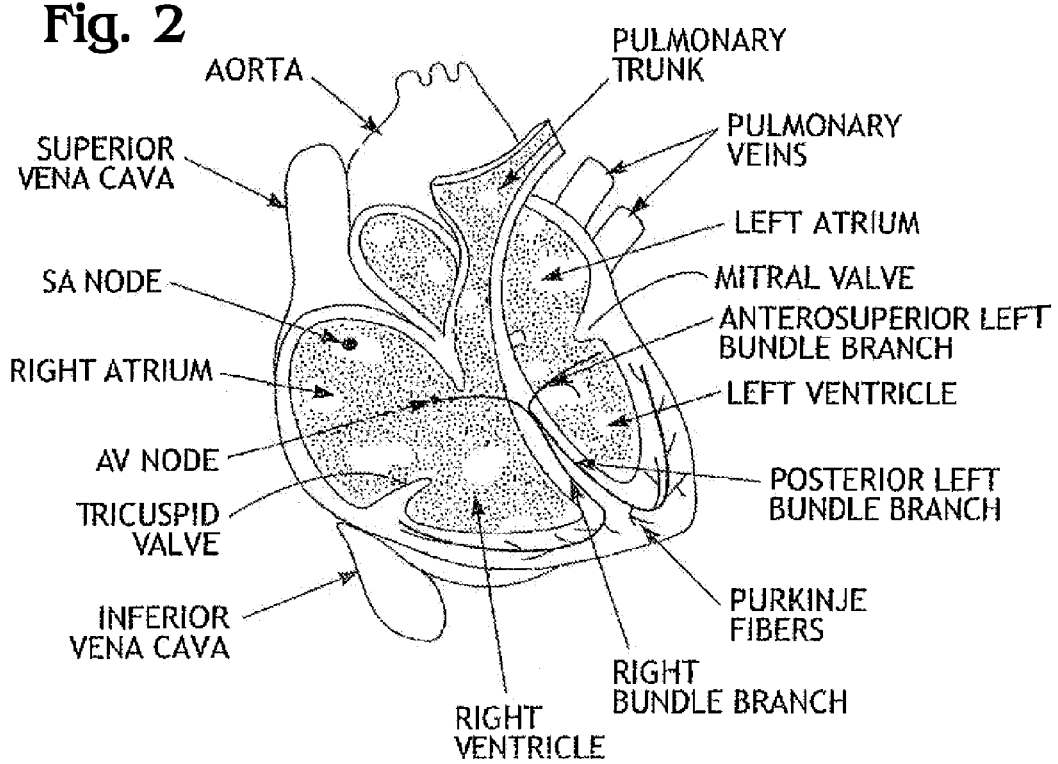
FIG. 2 is a cutaway view of the heart from the front, or anterior, perspective.
Figure 3:
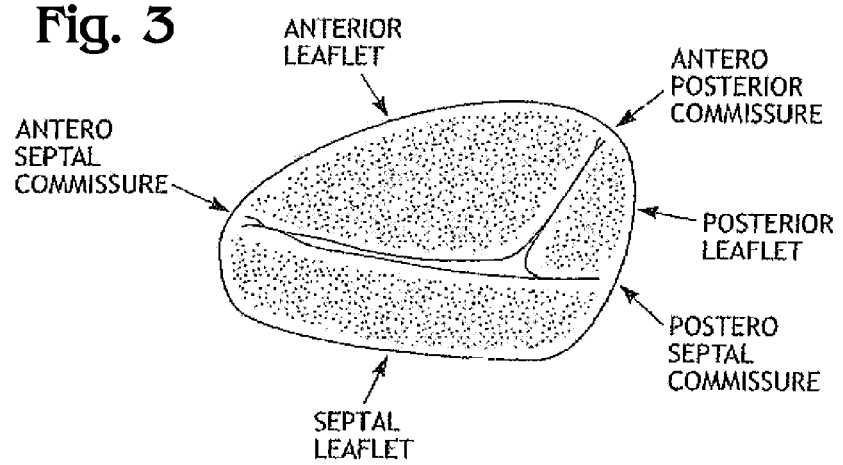
FIG. 3 is a schematic plan view of the tricuspid annulus with typical orientation directions noted as seen from the inflow side.
Figure 4:
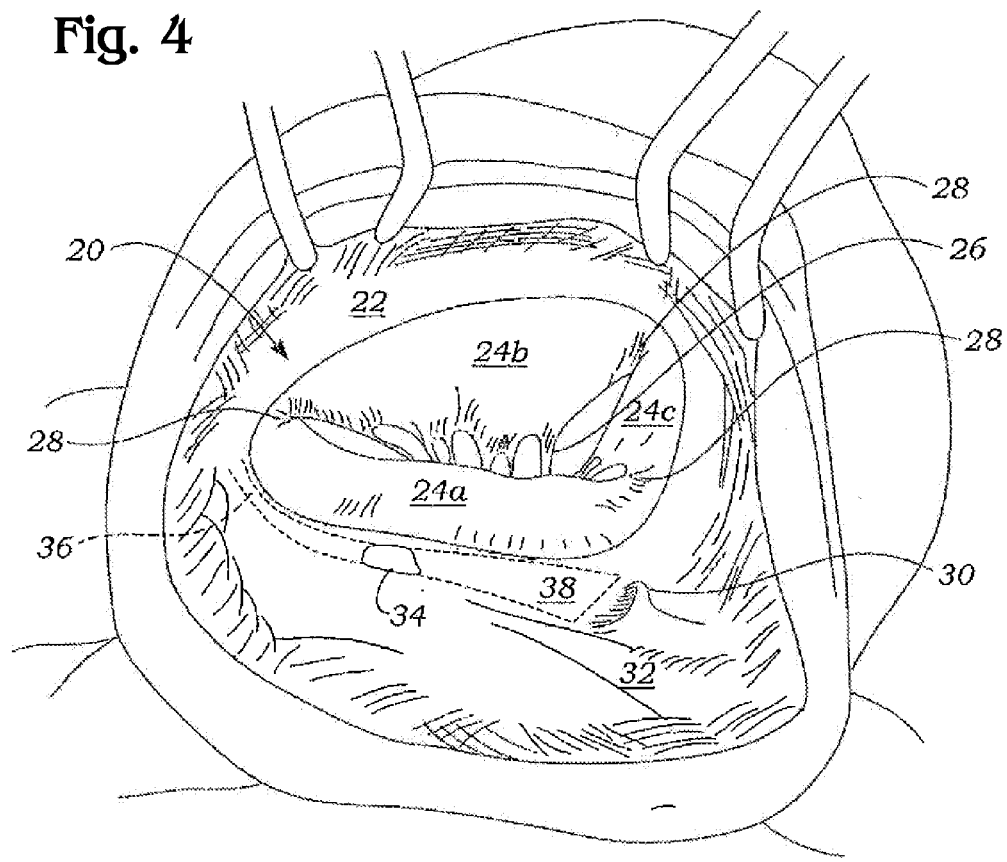
FIG. 4 is a plan view of the native tricuspid valve and surrounding anatomy from the inflow side.
Figure 5A:
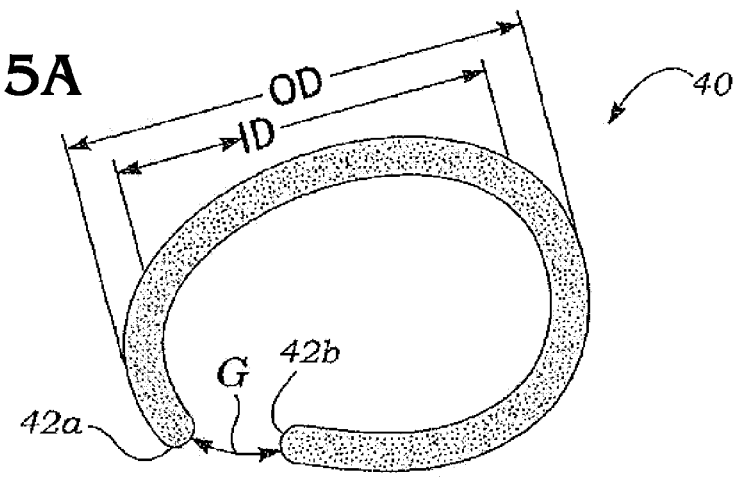
FIGS. 5A and 5B are plan and septal elevational views, respectively, of a planar tricuspid annuloplasty ring of the prior art.
Figure 5B:
Figure 6:
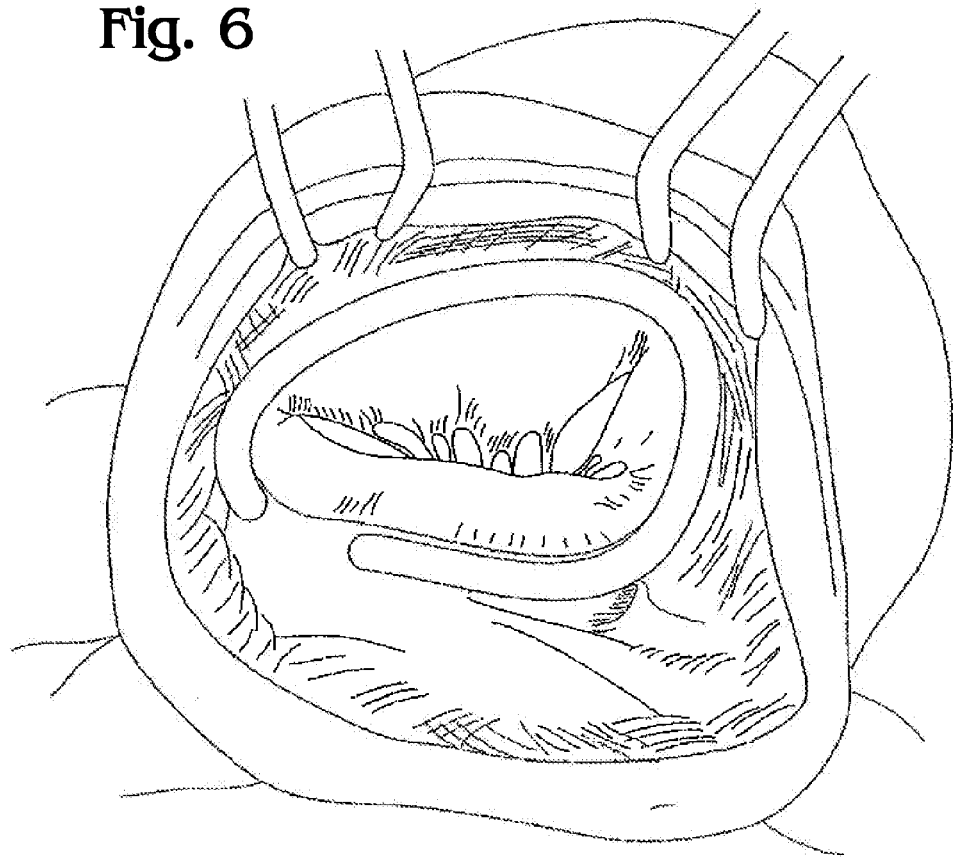
FIG. 6 is a plan view of the native tricuspid valve and surrounding anatomy from the inflow side with the annuloplasty ring of FIGS. 5A-5B implanted.

Embodiments of a tricuspid ring according to the present disclosure can at least partially restore the correct anatomy of the tricuspid valve annulus and/or the right ventricle. Tricuspid rings according to the present disclosure can be configured to be stiff or rigid in the XY plane (e.g., the plane of the annulus) and semi-flexible along the Z axis. The stiffness in the XY plane can allow embodiments of the disclosed tricuspid ring to resize the native valve annulus, such as by reshaping a dilated tricuspid valve that is regurgitating. The semi-flexibility along the Z axis can allow some embodiments of a tricuspid ring to conform to the natural shape of the native annulus, thereby reducing stress on the sutures securing the tricuspid ring in place. Tricuspid rings of the present disclosure can thereby reduce the likelihood of dehiscence in some embodiments.

The term "Z axis" refers to a line generally perpendicular to the ring that passes through the area centroid of the ring when viewed in plan view. "Axial" or "along the Z axis" or "in the direction of the Z axis" can also be viewed as being parallel to the direction of blood flow within the valve orifice and thus within the ring when implanted therein. Stated another way, the implanted tricuspid ring orients about a central flow axis aligned along an average direction of blood flow through the tricuspid annulus.

One embodiment of a tricuspid ring 700 according to the present disclosure is shown in FIGS. 7-13. FIG. 7 shows the tricuspid ring 700 in plan view and FIGS. 8-9 illustrate perspective views of the tricuspid ring 700. Tricuspid ring 700 can be generally C-shaped in the XY plane, having two free ends 702, 704, separated by a gap 703 as seen in FIG. 7. The length of the gap 703 can range from about 10% to about 60% of the labeled size of the tricuspid ring. In some embodiments, the length of the gap 703 can be from about 40% to about 50% of the labeled size of the tricuspid ring.

In some embodiments, the tricuspid ring can be substantially flat in the XY plane (e.g., substantially all points of the ring can be located at the same height on the Z axis). In other embodiments, as seen in FIGS. 8-9, the tricuspid ring 700 can have a saddle shape or a bimodal saddle shape in the Z axis, with at least one high point 706 and at least one low point 708. The terms "high" and "low" are being applied for convenience to the orientation seen in FIG. 8. The "high" points 706 are seen positioned below the "low" point 708 in the orientation seen in FIG. 9. Embodiments of the tricuspid ring 700 having a saddle shape can be configured to conform to the natural (e.g., not diseased) shape of the native valve annulus.

Generally, tricuspid rings of the present disclosure can be formed of an inner core that is overmolded with a material such as silicone. In some embodiments, a tricuspid ring can further be covered with a biocompatible flexible layer. For example, the biocompatible flexible layer can be a fabric layer, such as a polyester weave or velour. Some embodiments of a tricuspid ring can comprise an inner core encapsulated by an elastomeric interface and an outer fabric covering. The inner core can extend substantially around the entire periphery of the ring body and can comprise a material such as stainless steel, titanium, Elgiloy (an alloy primarily including Ni, Co, and Cr), cobalt chromium alloys (e.g., MP-35), Nitinol, polyester (e.g., Mylar), polymers, PET, PEEK, polycarbonate, PTFE, polysulfone, polyphenylsulfone, and/or combinations thereof. Any material suitable to support the annulus while allowing for the rigidity in the XY plane and semi-rigidity along the Z axis can be used.

Figure 10:
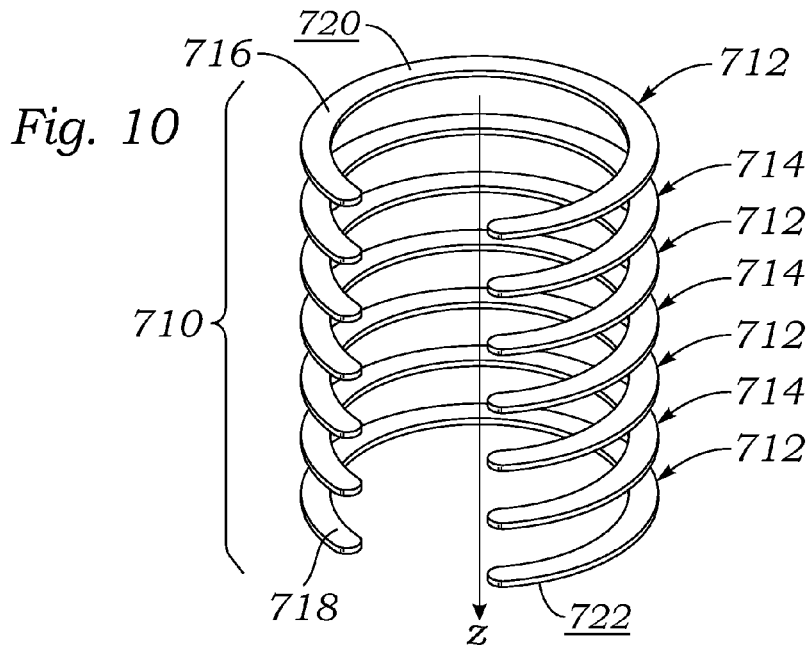
FIG. 10 is an exploded perspective view of the core of a tricuspid ring according to the present disclosure.

In some embodiments, the core can comprise a plurality of layers that are held together by the overmolding material. For example, FIG. 10 shows an exploded view of the core 710 of tricuspid ring 700, comprising a plurality (e.g., a stack) of layers 712, 714 stacked adjacent one another along the Z axis. In some embodiments, the core 710 of the tricuspid ring can comprise a plurality of bands or layers 712 with interface layers 714 between each of the layers 712, or between a selected number of layers 712. In some embodiments, the layers 712 can comprise one or more of the metals or metal alloys listed above, while the interface layers 714 can comprise one or more of the polymer materials listed above. For example, the core 710 can comprise a plurality of Elgiloy layers 712 with a relatively thin layer 714 of polyester between every two Elgiloy layers 712, with Elgiloy forming both the top layer 716 and the bottom layer 718 of the core 710 in some embodiments. In other embodiments, interface layers 714 can form the top and/or bottom layer of the stack.

Figure 11:
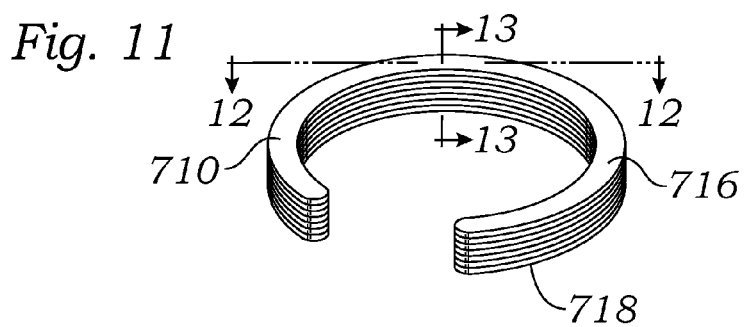
FIG. 11 is a perspective view of the assembled core of FIG. 10.

FIG. 11 shows the assembled core 710 of tricuspid ring 700. While FIGS. 10 and 13 show seven layers forming the core 710 (e.g., four layers 712 and three layers 714), more or fewer layers can be used.

In some embodiments, the interface layers 714 can reduce wear between the layers 712. In addition to or instead of the interface layers 714, at least one of the layers 712 can be coated with a lubricious polymer (e.g., PTFE) on at least a portion of the surface of layer or layers 712. For example, in specific embodiments, the layers 712 can be coated with a lubricious polymer on the surfaces adjacent other layers 712, while the top surface 720 of the top layer 716 and the bottom surface 722 of the bottom layer 718 can remain free of such lubricious polymer coating. In other embodiments, a coating of a lubricious polymer over substantially the entire surface of each layer 712 can replace the interface layers 714.

Forming the core 710 from a plurality of layers stacked in the Z direction can provide greater flexibility along the Z axis and yet provides sufficient rigidity in the XY plane. In some specific embodiments, each of the layers 712, 714 can have substantially the same thickness (indicated by "t" in FIG. 13). In some embodiments, each of the layers 712, 714 can be less than about 0.1 inches thick. In some embodiments, each of the layers 712, 714 can be less than about 0.01 inches thick. In one specific embodiment, each of the layers 712, 714 can be about 0.009 inches thick. In some embodiments, the width (indicated by "w" in FIG. 13) of each of the layers 712, 714 can be less than about 0.1 inches. In one specific embodiment, the width of each of the layers 712, 714 can be about 0.070 inches.

Figure 12:
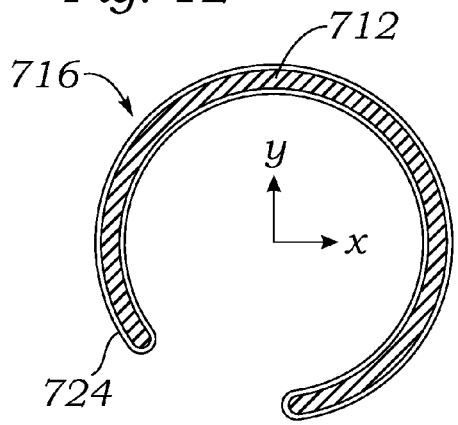
FIG. 12 is a top cross sectional view of the core of FIG. 11, taken along line 12-12 in FIG. 11.
Figure 13:
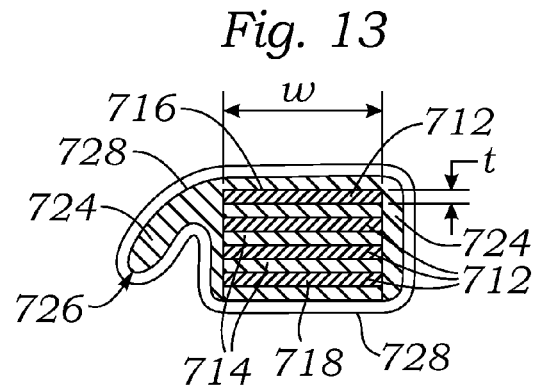
FIG. 13 is a cross sectional view of the core of FIG. 11, taken along line 13-13 in FIG. 11.

In some embodiments, the core 710 can be overmolded with an elastomeric interface 724, as seen in FIGS. 12-13. FIG. 12 shows a cross section of the top layer 716, with the Elgiloy layer 712 being encased by an elastomeric interface 724, such as a silicone overmold or silicone tubing. The elastomeric interface 724 can be silicone rubber molded around the core, or a similar expedient. The elastomeric interface 724 can provide bulk to the ring for ease of handling and implant, and can facilitate passage of sutures. As seen in FIG. 13, the elastomeric interface 724 can help to hold together the layers 712, 714 of the core 710 of tricuspid ring 700. For example, the elastomeric interface 724 can hold the layers 712, 714 of the core together without the need for welding or adhesives in some embodiments. In some embodiments, adhesive can optionally be provided between adjacent layers 712, 714 to help hold the stack together. While silicone provides an exemplary material for the elastomeric interface 724, any material that has a sufficiently low hardness (e.g., about 60 Shore A or less) so as not to significantly impact the flexibility of the core 710 can be used.

In some embodiments, as seen in FIG. 13, the elastomeric interface 724 can be formed with an inwardly extending radial flange forming a sewing cuff 726 (not shown in FIGS. 7-12) that can be configured to aid in suturing the tricuspid ring 700 in place within the native valve.

Tricuspid ring 700 can also include an outer fabric or cloth covering 728 enveloping the elastomeric interface 724 and the core 710. The fabric covering 728 can be any biocompatible material such as, for example, Dacron® (polyethylene terepthalate).

Figure 14:
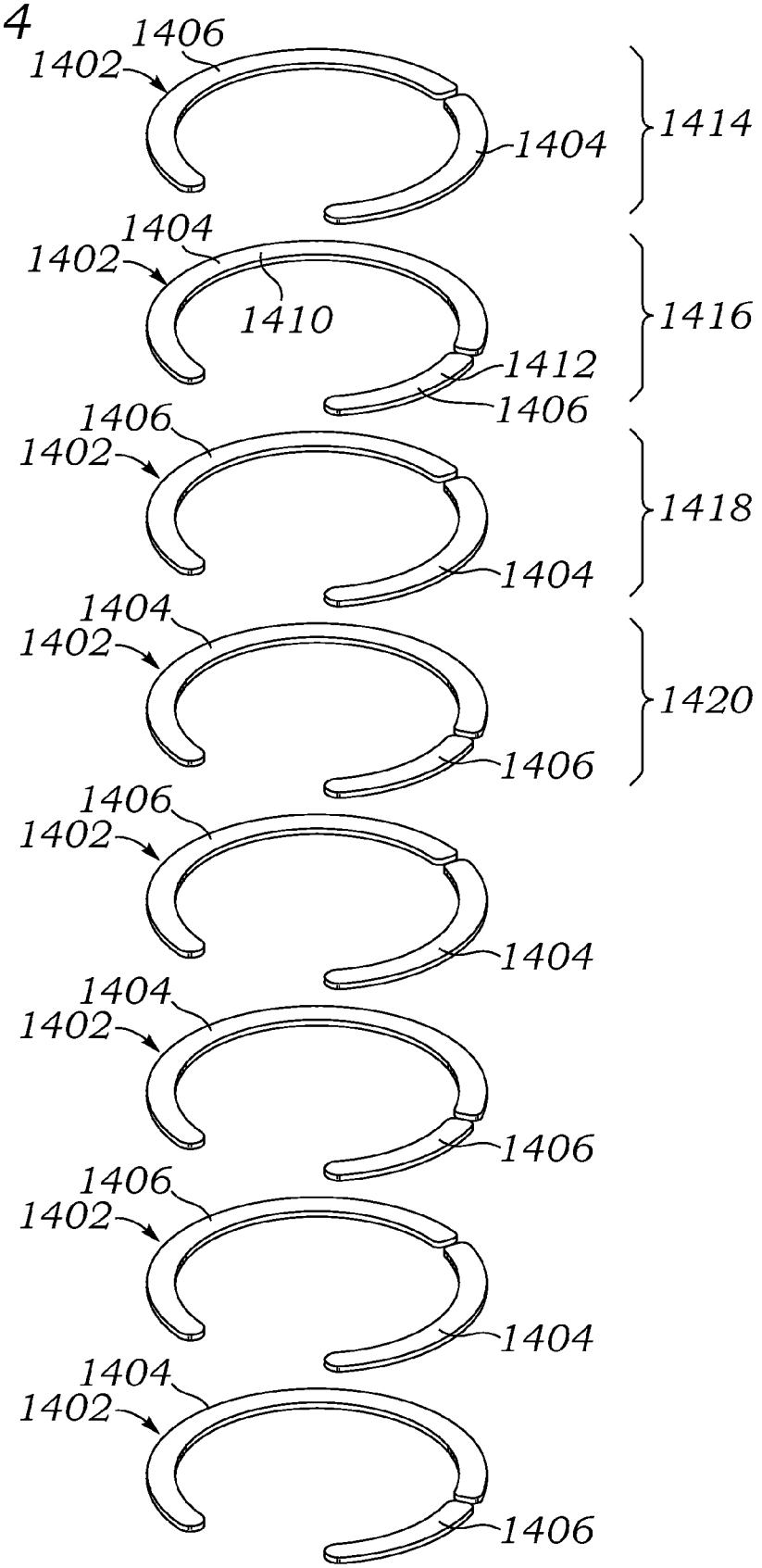
FIG. 14 is an exploded perspective view of the core of a tricuspid ring according to the present disclosure.
Figure 15:
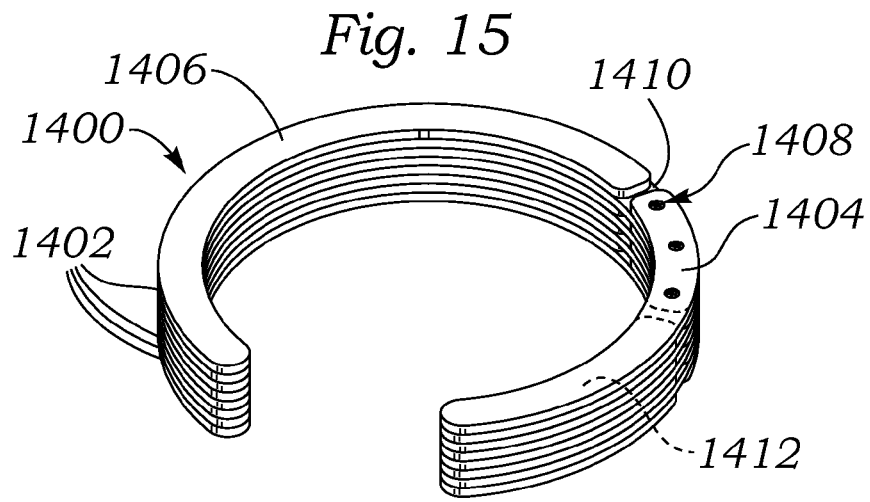
FIG. 15 is a perspective view of the assembled core of FIG. 14.

FIGS. 14-15 illustrate another embodiment of a core 1400 for a tricuspid ring that can be configured to provide rigidity in the XY plane and flexibility along the Z axis, according to the present disclosure. As best seen in FIG. 14, the core 1400 can comprise a plurality of layers 1402 (e.g., a stack). Each layer 1402 can comprise a structural portion 1404 (comprising, e.g., Elgiloy) and a shim portion 1406 (comprising, e.g., polyester). The structural portions 1404 can comprise, for example, any of the materials discussed above as suitable for the layers 712 of tricuspid ring 710. Similarly, the shim portions 1406 can comprise, for example, any of the materials discussed above as suitable for the interface layers 714 of tricuspid ring 710. Structural portions 1404 can lend structure and mechanical properties (e.g., stiffness in the XY plane) to the tricuspid ring, while shim portions 1406 can serve to add lubricity between the layers' 712 structural portions 1404, thereby contributing to flexibility along the Z axis.

As shown in FIG. 15, the layers 1402 can be stacked on one another to form core 1400. The layers 1402 can be welded together, such as by spot welding or resistance welding. Other suitable techniques can also be used to hold the layers together. As an example, FIG. 15 shows weld points 1408 securing the structural portion 1404 of the top layer to the structural portion 1410 of the next layer down.

Adjacent layers 1402 can be oriented differently with respect to one another and/or the structural portions 1404 and shim portions 1406 can be different sizes in adjacent layers 1402. For example, the top layer 1414 of the core 1400 can be configured such that the shim portion 1406 is on the left and the structural portion 1404 is on the right, while the second layer 1416 can be configured just the opposite, such that the shim portion 1412 is on the right and the structural portion 1410 is on the left.

Further, the structural portion 1404 of any given layer can be bigger than the shim portion 1406 of any adjacent layer. For example, the structural portion 1404 of top layer 1414 can be sized such that it is smaller than the structural portion 1410 of the second layer 1416 and larger than the shim portion 1412 of the second layer 1416. The shim portion 1406 of the top layer 1414 can be sized such that it is smaller than the structural portion 1410 of the second layer 1416 and larger than the shim portion 1412 of the second layer 1416. In this manner, the structural portions of adjacent layers, e.g., layers 1414, 1416 (and etc. down the stack) can overlap. Thus, the structural portion 1404 of any given layer can be arranged to overlap a portion of the structural portion 1404 of any adjacent layer. For example, a portion of the structural portion 1404 of the top layer 1414 can overlap with and contact a portion of the structural portion 1410 of the second layer 1416. In some embodiments, the shim portion 1406 of any given layer and the shim portion 1406 of any adjacent layer do not overlap. For example, the shim portion 1406 of the top layer 1414 does not overlap the shim portion 1412 of the second layer 1416. Weld points 1408 can be positioned in the areas of overlap between adjacent structural portions. The third layer 1418 can be sized and oriented substantially the same as the top layer 1414 and the fourth layer 1420 can be sized and oriented substantially the same as the second layer 1416. The layers 1402 can alternate in this pattern for the remainder of the layers 1402 in the core 1400. While FIG. 14 shows eight layers 1402 forming the core 1400, more or fewer layers can be used.

Figure 16:
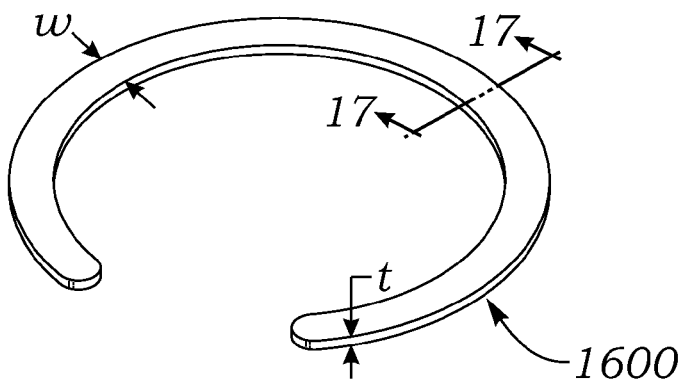
FIG. 16 is a perspective view of another embodiment of a core of a tricuspid ring according to the present disclosure.
Figure 17:
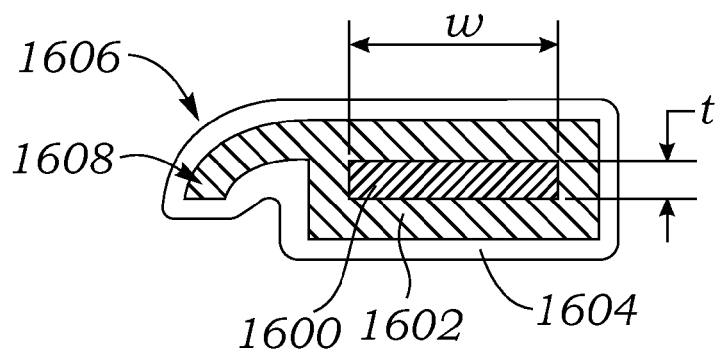
FIG. 17 is a cross sectional view of the core of FIG. 16, taken along line 17-17 in FIG. 16.

FIGS. 16-17 illustrate another embodiment of a core 1600 for a tricuspid ring that can be configured to provide rigidity in the XY plane and flexibility along the Z axis, according to the present disclosure. FIG. 16 shows a perspective view of core 1600, while FIG. 17 shows a cross sectional view of the tricuspid ring, taken along line 17-17 in FIG. 16.

Core 1600 can comprise a solid layer of material (e.g., a single piece core), such as titanium. Core 1600 can comprise any biocompatible metal and/or plastic. Core 1600 can be configured to have a substantially rectangular cross section with a relatively large width (indicated by "w") and a relatively small thickness (indicated by "t"). The thickness and/or width of the core 1600 can be varied to alter the stiffness of the tricuspid ring, as desired for particular applications. For example, stiffness in the XY plane is a function of the area moment of inertia of the cross section. The area moment of inertia for the XY plane is proportional to the thickness t and to the width w cubed for the rectangular cross section shown, according to the following equation:

$$I_{xy}=(1/12)*t*w^3$$

The stiffness along the Z axis is also a function of the area moment of inertia of the cross section. The area moment of inertia for the Z direction is proportional to the width w and to the thickness t cubed for the rectangular cross section shown, according to the following equation:

$$I_z=(1/12)*w*t^3$$

Thus, increasing the width of the core with respect to the thickness can increase stiffness in the XY plane relative to the stiffness along the Z axis. Similarly, decreasing the width of the core with respect to the thickness can decrease the stiffness in the XY plane relative to the stiffness along the Z axis.

In some embodiments, the stiffness in the XY plane can be much greater than the stiffness along the Z axis. For example, the stiffness in the XY plane can be from about 10 times greater to about 100 times greater than the stiffness along the Z axis. In one specific embodiment, the stiffness in the XY plane can be about 25 times greater than the stiffness along the Z axis. For example, one embodiment of a tricuspid ring core 1600 can have a width of about 0.100 inches and a thickness of about 0.020 inches. In this embodiment, the area moment of inertia in the XY plane is about $1.67 \times 10^{-6}$ and the area moment of inertia in the Z direction is about $6.67 \times 10^{-8}$. Thus, the stiffness in the XY plane can be about 25 times greater than the stiffness in the Z direction.

The core 1600 can also be provided with different shaped cross sections, with parameters such as width and thickness being varied to impart the desired stiffness in the XY plane and/or along the Z axis.

As seen in FIG. 17, the core 1600 covered with an elastomeric interface layer 1602 (e.g., a silicone overmolding) and a fabric covering 1604 (e.g., Dacron®), which are not shown on the core 1600 in FIG. 16, for clarity, to form tricuspid ring 1606. Suitable materials for the elastomeric interface layer 1602 and the fabric covering 1604 are described above. The tricuspid ring 1606 can optionally include a sewing cuff 1608 for securing the tricuspid ring in place in a patient's native valve.

FIGS. 18-21 illustrate multiple views of a tricuspid ring 1800 having a saddle shape including at least one high point 1802 and at least one low point 1804 and two free ends 1806, 1808 according to the present disclosure. Dimensions of the ring can be varied to create a set of rings in different sizes. For example, dimension A can range from about 0.5 inches to about 2 inches. Dimension B can range from about 0.5 inches to about 1.5 inches. Dimension C can range from about 0.05 inches to about 0.25 inches. Angle D can range from about 15 degrees to about 35 degrees. Dimension E can range from about 0.25 inches to about 1 inch. Dimension F can range from about 0.05 inches to about 0.25 inches. The radius of curvature G can range from about 0.5 inches to about 2 inches. The radii of curvature H and L can range from about 0.25 inches to about 1.5 inches. Dimension I can range from about 0.1 inches to about 1 inch. Dimension J can range from about 0.1 inches to about 0.3 inches. Dimension K can range from about 0.25 inches to about 1.5 inches. The provided ranges are merely exemplary embodiments, and can be increased or decreased in other embodiments.

Disclosed tricuspid rings can possess a varying flexibility around its periphery. For example, the ring can be stiffer adjacent the first free end than adjacent the second free end, and can have a gradually changing degree of flexibility for at least a portion in between. For instance, the ring can be relatively stiff adjacent the first free end, while the remainder of the ring body gradually can become more flexible through the remainder of the ring towards the second free end.

It should also be understood that features of the present tricuspid ring can also be applicable and beneficial to rings for other of the heart's annuluses, such as the mitral valve annulus.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A tricuspid ring for use in an annuloplasty procedure, comprising:
   an inner core comprising a plurality of parallel and separate layers stacked along and defining a periphery around a Z axis, each of the layers comprising a coplanar structural portion and a lubricious shim portion, and wherein the structural portion of each layer is a separate and distinct element from the structural portions of the other layers, wherein at least one weld point couples the layers of the inner core together;
   an elastomeric interface at least partially covering the inner core; and
   a biocompatible flexible layer at least partially covering the elastomeric interface.

2. The tricuspid ring according to claim 1, wherein the tricuspid ring is configured to be significantly more rigid in bending in the XY plane than it is in bending in any Z axis plane.

3. The tricuspid ring according to claim 1, wherein each of the plurality of layers is substantially the same size.

4. The tricuspid ring according to claim 1, wherein the structural portions comprise at least one material selected from the group consisting of Elgiloy, Nitinol, titanium, stainless steel, cobalt chromium, and alloys thereof.

5. The tricuspid ring according to claim 1, wherein the shim portions comprise at least one material selected from the group consisting of polyester, PET, PEEK, PTFE, polycarbonate, polysulfone, and polyphenylsulfone.

6. The tricuspid ring according to claim 1, wherein the structural portions of adjacent layers are arranged to at least partially overlap.

7. The tricuspid ring according to claim 1, wherein the plurality of layers comprises a plurality of repeating pairs of layers, each pair of layers comprising a first layer and a second layer, wherein the first layers are identical and the second layers are identical.

8. The tricuspid ring according to claim 1, wherein the structural portion of any layer is bigger than the shim portion of any adjacent layer.

9. The tricuspid ring according to claim 8, wherein the structural portion of any layer is arranged to overlap a portion of the structural portion of any adjacent layer.

10. The tricuspid ring according to claim 9, wherein the shim portion of any layer and the shim portion of any adjacent layer do not overlap.

11. The tricuspid ring according to claim 1, further comprising a sewing cuff.

12. The tricuspid ring according to claim 1, wherein the tricuspid ring is configured such that a gap exists between a first free end and a second free end, the tricuspid ring having a saddle shape having at least one high point and at least one low point.

13. An annuloplasty ring, comprising:
    an inner core comprising a plurality of parallel and separate layers stacked along and defining a periphery around a Z axis, each of the layers having a structural portion that extends around the periphery a different distance than the structural portion in any adjacent layer such that the structural portion in adjacent layers partially overlap, and each layer having a coplanar shim portion that extends between adjacent structural portions where they do not overlap.

14. The annuloplasty ring of claim 13, wherein the structural portions in adjacent layers are adhered together where they partially overlap.

15. The annuloplasty ring of claim 13, wherein the structural portions in adjacent layers are welded together where they partially overlap.

16. The annuloplasty ring of claim 13, wherein the shim portions comprise at least one material selected from the group consisting of polyester, PET, PEEK, PTFE, polycarbonate, polysulfone, and polyphenylsulfone.

17. The annuloplasty ring of claim 13, wherein the ring is configured such that a gap exists between a first free end and a second free end, and in any one layer the structural portion extends from one of the first or second free end while the shim portion extends from the other of the first or second free end, and the end from which the structural portion extends alternates in sequential layers.

18. The annuloplasty ring of claim 13, wherein the plurality of layers comprises a plurality of repeating pairs of layers, each pair of layers comprising a first layer and a second layer, wherein the first layers are identical and the second layers are identical.

19. An annuloplasty ring, comprising:
    an inner core comprising a plurality of parallel and separate layers stacked along and defining a periphery around a Z axis, each of the layers having a relatively rigid structural portion that extends around the periphery a first distance and a coplanar shim portion that extends around the periphery a second distance different than the first distance, wherein the ring is configured such that a gap exists between a first free end and a second free end, and in any one layer the structural portion extends from one of the first or second free end while the shim portion extends from the other of the first or second free end, and the end from which the structural portion extends alternates in sequential layers.

20. The annuloplasty ring of claim 19, wherein the structural portion in each of the layers extends around the periphery a different distance than the structural portion in any adjacent layer such that the structural portion in adjacent layers partially overlap, and the shim portion in each layer extends between adjacent structural portions where they do not overlap.

21. The annuloplasty ring of claim 20, wherein the structural portions in adjacent layers are adhered together where they partially overlap.

22. The annuloplasty ring of claim 20, wherein the structural portions in adjacent layers are welded together where they partially overlap.

23. The annuloplasty ring of claim 19, wherein the shim portions comprise at least one material selected from the group consisting of polyester, PET, PEEK, PTFE, polycarbonate, polysulfone, and polyphenylsulfone.

24. The annuloplasty ring of claim 19, wherein the plurality of layers comprises a plurality of repeating pairs of layers, each pair of layers comprising a first layer and a second layer, wherein the first layers are identical and the second layers are identical.

* * * * *